United States Patent [19]

Weder et al.

[11] Patent Number: 5,152,923
[45] Date of Patent: Oct. 6, 1992

[54] PROCESS FOR THE PRODUCTION OF A NANOEMULSION OF OIL PARTICLES IN AN AQUEOUS PHASE

[75] Inventors: Hans G. Weder, Saumerstrasse 68, CH-8800 Thalwil; Matthias Mütsch, Zurich, both of Switzerland

[73] Assignee: Hans Georg Weder, Thalwil, Switzerland

[21] Appl. No.: 541,501

[22] Filed: Jun. 21, 1990

[30] Foreign Application Priority Data

Jun. 26, 1989 [CH] Switzerland ............... 2374/89

[51] Int. Cl.$^5$ ............................................. B01J 13/00
[52] U.S. Cl. .................................... 252/312; 252/314; 424/455; 514/938; 435/240.3; 435/240.31
[58] Field of Search ................ 252/312, 314; 424/455; 514/938; 435/240.3, 240.31

[56] References Cited

U.S. PATENT DOCUMENTS

| | | | |
|---|---|---|---|
| 4,794,000 | 12/1988 | Ecanow | 424/457 |
| 5,021,381 | 6/1991 | Burroway et al. | 502/117 |

FOREIGN PATENT DOCUMENTS

| | | |
|---|---|---|
| 1249454 | 9/1967 | Fed. Rep. of Germany . |
| 2938807 | 7/1982 | Fed. Rep. of Germany . |
| WO88/08301 | 11/1988 | PCT Int'l Appl. . |

OTHER PUBLICATIONS

*Biochemstry,* by L. Stryer, W. H. Freeman and Company, New York, New York, 1988, pp. 288–290.

*Primary Examiner*—Richard D. Lovering
*Assistant Examiner*—N. Bhat
*Attorney, Agent, or Firm*—Young & Thompson

[57] ABSTRACT

An aqueous phase, an oil of a triglyceride or fatty acid ester, and, per part by weight of oil 0.05 to 0.4 part by weight of an amphoteric emulsifier are mixed together and processed in a high-pressure homogenizer into a nanoemulsion of less than 200 nm sized oil particles. The emulsifier, exhibiting in the aqueous phase a lamellar liquid-crystalline structure, is preferably a glycerophosphatide of the formula:

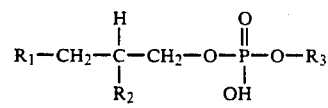

wherein, $R_1$ and $R_2$ mean acyloxy and/or alkyl or alkenyl ether. $R_3$ is a tri-lower-alkyl ammonio or amino-substituted lower alkyl. The resultant nanoemulsion is stable for a period of several months and does not contain any toxic emulsifier materials. Therefore, it can be advantageously utilized as a vehicle for active agents, for example medicines and/or cosmetic ingredients.

11 Claims, No Drawings

PROCESS FOR THE PRODUCTION OF A NANOEMULSION OF OIL PARTICLES IN AN AQUEOUS PHASE

BACKGROUND OF THE INVENTION

The invention relates to a process for the production of a nanoemulsion of less than 200 nm sized oil particles of a triglyceride or fatty acid ester in an aqueous phase by means of a high-pressure homogenizer.

Such a nanoemulsion can be characterized as a colloid-highly disperse two-phase system, and it can be clearly distinguished, based on laser light scattering measurements and electron microscope images, from associations (micelles) and solubilized products (micellar solutions=swollen micelles), as they are described, for example, in P. H. List, B. W. Müller and E. Nürnberg, "Emulsionen" [Emulsions], in "Arzneiformenlehre" [Manual of Pharmaceuticals] 1982, Wissenschaftliche Verlagsgesellschaft mbH [publishers], Stuttgart, pages 141-176. The nanoemulsion is defined with respect to coarsely disperse systems by a particle size of less than 200 nm.

So-called "microemulsions" have been disclosed in H. Sucker, P. Fuchs and P. Speiser, "Dermatica", in "Pharmazeutische Technologie" [Practice of Pharmacy] 1978, Georg Thieme publishers, Stuttgart, pages 663-665. Since the meaning of the term "microemulsion", however, has thus far not as yet been exactly clarified, the term nanoemulsion is employed herein for denoting an emulsion with less than 200 nm sized oil particles.

In the conventional preparation of "microemulsions", highly concentrated tenside-cotenside mixtures are needed in order to effect minimum surface tension and to ensure physical stability of the emulsion. The most troublesome drawbacks from the viewpoint of pharmaceuticals are the high tenside-cotenside concentrations necessary for preparation, and the toxicity of the known emulsifier complexes. Due to the aforementioned disadvantages, practical use of the "microemulsions", for example as medicine vehicles for lipophilic active agents, or their usage for parenteral alimentation could not be considered heretofore.

SUMMARY OF THE INVENTION

It is an object of this invention to make available a process of the type discussed above permitting the production of stable nanoemulsions without the use of highly concentrated tenside-cotenside complexes.

The process of this invention, solving the aforedescribed problem, is characterized in that the aqueous phase, the oil and, per part by weight of oil, 0.05-0.4 part by weight of an amphoteric emulsifier exhibiting a lamellar liquid-crystalline structure in the aqueous phase are mixed together and processed into the nanoemulsion in the high-pressure homogenizer.

DETAILED DESCRIPTION OF THE INVENTION

It is possible with the aid of the process according to this invention to prepare reproducible nanoemulsions which are stable for at least a period of several months, which are harmless from a toxicological viewpoint, and which can thus be utilized as medical vehicles, in parenteral preparations, in cosmetic preparations, and in nutrient solutions (cell culture media for biotechnology). Such a nanoemulsion can also be used as a carrier for a compound having an oxygen-transfer function, and thus can serve as a blood substitute.

Such a substance or oxygen carrier capable of binding molecular oxygen is, for example, oxygen-saturated hemoglobin. The oxygen carrier, however, can also be present, of course, in the nanoemulsion without the oxygen load.

The amphoteric emulsifier utilized in the process of this invention which can preferably be a biological or biologically produced emulsifier can suitably be a glycerophosphatide of the formula

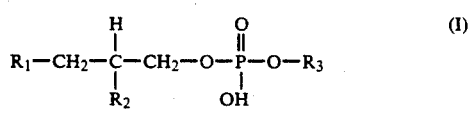

wherein $R_1$ and $R_2$ mean acyloxy and/or alkyl or alkenyl ether, and $R_3$ is tri-lower-alkyl ammonio, e.g. trimethylammonio, or amino-substituted lower alkyl, for example 2-trimethylammonioethyl (cholinyl). $R_1$ and $R_2$ are preferably acyloxy, i.e. ester-linked fatty acid residues; alkyl or alkenyl ethers, i.e. ether-linked fatty acid residues are, however, likewise possible. $R_3$ is preferably 2-trimethylammonioethyl or 2-aminoethyl. A glycerophosphatide of Formula (I) wherein $R_1$, $R_2$ and $R_3$ have the last-mentioned meanings is, for example, a natural lecithin, e.g. egg lecithin, or lecithin from soybeans ($R_3$=2-trimethylammonioethyl), or a natural cephalin, e.g. egg cephalin, or cephalin from soybeans ($R_3$=2-aminoethyl).

The emulsifier is to exhibit in the aqueous phase a maximally extensively ideal lamellar liquid-crystalline structure, forming the interface between the external aqueous phase and the internal oil phase. The physical conditions for a stable emulsion (such emulsions display no coalescence) are: maximum specific interface and maximum interfacial energy of the particles, as well as minimum interfacial tension, which means practically that particles of a minimum size, for example 50-100 nm, should be produced having homogeneous size distribution. In the nanoemulsion prepared in accordance with the process of this invention, coalescence is prevented by maintaining the indicated weight ratio of emulsifier/oil of 0.05-0.4, preferably 0.1-0.35. Additionally, the particle density, i.e. the total lipid concentration (emulsifier+oil) is to be preferably at most 20% by weight, with particle sizes of 50-100 nm. Furthermore, attention should be directed suitably to intensive interaction of the molecules of the lamellar emulsifier structure with those of the oil phase.

Further preferred glycerophosphatides (as emulsifiers) are also synthetic lecithins ($R_3$=2-trimethylammonioethyl) and synthetic cephalins ($R_3$=2-aminoethyl) of Formula (I) wherein $R_1$ and $R_2$ mean identical acyloxy residues, for example lauroyloxy, oleoyloxy, linoyloxy, linoleoyloxy, or arachidoyloxy, for example, dilauroyl, dimyristoyl, dipalmitoyl, distearoyl, dioleoyl, dilinoyl, dilinoleoyl, or diarachidoyl lecithin or cephalin, or $R_1$ and $R_2$ mean different acyloxy residues, e.g. $R_1$ is palmitoyloxy and $R_2$ is oleoyloxy, for example 1-palmitoyl-2-oleoyl lecithin or cephalin, or $R_1$ and $R_2$ mean identical alkoxy residues, e.g. tetradecyloxy or hexadecyloxy, for example ditetradecyl or dihexadecyl lecithin or cephalin, $R_1$ means alkenyl and $R_2$ means acyloxy, e.g. a plasmalogen ($R_3$=trimethylammonioethyl), or $R_1$ is acyloxy, e.g. myristoyloxy or palmitoyloxy and $R_2$ is hydroxy, e.g. natural or synthetic lysolecithin or lysocephalin, for example 1-myristoyl or 1-palmitoyl lysolecithin or cephalin. As mentioned above, an ether linkage can also take the place of the ester linkage herein.

A suitable lipid is furthermore a lipid of Formula (I) wherein $R_1$ is an alkenyl residue, $R_2$ is an acylamido residue, and $R_3$ is 2-trimethylammonioethyl (choline residue). Such a lipid is known under the name of sphingomyelin.

A suitable lipid is furthermore a lysolecithin analog, for example 1-lauroyl-1,3-propanediol-3-phosphorylcholine, a monoglyceride, e.g. monoolein or monomyristin, a cerebroside, a ganglioside or a glyceride which does not contain a free or esterified phosphoryl or phosphonyl group in the 3-position. Such a glyceride is, for example, a diacyl glyceride or a 1-alkenyl-1-hydroxy-2-acyl glyceride with the aforementioned acyl or alkenyl groups, wherein the 3-hydroxy group is etherified by one of the mentioned carbohydrate residues, e.g. a galactosyl residue, for example a monogalactosyl glycerol.

Another suitable lipid is furthermore a neutral lipid contained in cellular membranes and soluble only in apolar organic solvents, for example in chloroform. Neutral lipids are, for instance, steroids, e.g. estradiol or sterols, e.g. cholesterol, $\beta$-sitosterol, desmosterol, 7-ketocholesterol or $\beta$-cholestanol, fat-soluble vitamins, e.g. vitamin A, for example vitamin $A_1$ or $A_2$, vitamin E, vitamin K, e.g. vitamin $K_1$ or $K_2$, or vitamin $D_2$ or $D_3$.

The oil utilized in the process of this invention can be a liquid fat of animal, vegetable or synthetic origin having the following general structure:

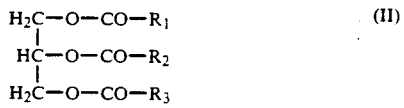

(II)

$R_1$, $R_2$ and $R_3$ represent saturated and unsaturated fatty acid residues (unbranched and branched) with variable chain lengths up to maximally $C_{24}$ including semisynthetic derivatives. The most usual pharmaceutical triglycerides are: peanut oil, soybean oil, cottonseed oil and "Miglyols".

The oil phase can furthermore consist of fatty acid esters. The fatty acid components can be the same fatty acids as described in connection with the triglycerides. The fatty acid esters contain alcohol residues with carbon chains from $C_1$ to $C_{24}$. The alcohols can be of unbranched, branched, as well as saturated and unsaturated structures. Synthetic derivatives of mono- and polyhydric alcohols are likewise included. Customary pharmaceutical fatty acid esters are: palmitic acid isopropyl ester, myristic acid isopropyl ester, oleic acid ethyl ester.

In general, the following procedure can be employed for producing a nanoemulsion:

An o/w pre-emulsion is obtained by simple shaking of the emulsifier/oil-water mixture for several minutes until, as determined visually, the entire amount of oil has been incorporated. The temperature herein is to be selected so that the process is performed above the phase transition temperature of the emulsifier (present in the liquid-crystalline structure).

The thus-obtained o/w pre-emulsion is transferred into a high-pressure homogenizer of commercially available origin and comminuted therein to the desired particle size. During this step, the temperature is maintained constant and again ranges above the transition temperature of the selected emulsifier.

Stable nanoemulsions having a defined, homogeneous particle size distribution are obtained by the correct selection of emulsifying time and pressure. Preferably, a chamber pressure of 500–1,000 bar is utilized, the degree of efficiency of which is affected by the chamber geometry of the high-pressure homogenizer employed.

The resultant nanoemulsions can be treated to be antimicrobial by pressurized steam sterilization (1 bar excess pressure, 20 minutes at 120° C.) or germ filtration (0.2 $\mu$m pore size).

The following means are employed for characterization of the thus-produced nanoemulsions:
optical evaluation: slight to strong opalescence of the preparation can be readily observed (suggestion of a particle size smaller than 200 nm),
laser nephelometry (particle size and homogeneity),
electron microscopy (freeze fracture and negative contrast technique; verification of laser nephelometry measurements and information on morphology of particles),
chemical analysis of the nanoemulsion components utilized.

EXAMPLE 1

Production of a 1–2% Strength Nanoemulsion with a Triglyceride

A round flask is charged with weighed amounts of 250 mg of the amphoteric emulsifier lecithin (fat-free) and 1,000 mg of soybean oil as the oil component. By adding ethanol (about 15 ml), the two compounds are dissolved and then the solvent is removed again by means of a rotary evaporator. The residue is filled up to 100 ml with physiological sodium chloride solution. The mixture is then shaken until the oil has been completely incorporated (visual evaluation).

This pre-emulsion is transferred to a high-pressure homogenizer of a commercially available origin and comminuted to the desired particle size of about 100 nm. Homogenization is carried out with a chamber pressure of 950 bar for a period of 20 minutes. This process is performed at a constant temperature of 35° C. This nanoemulsion is stable over several months. The product is characterized in Table 1 set forth below.

TABLE 1

| 1. Visual: | slightly milky, opalescent, transparent in backlight | |
|---|---|---|
| 2. Chemical: | | |
| Component | Concentration (mg/ml) in Physiological Sodium Chloride Solution | |
| | Weighed Amount | Measured in Nanoemulsion |
| Lecithin | 2.5 | 2.53 ± 0.07[1] |
| Soybean Oil | 10.0 | 9.83 ± 0.22[2] |
| 3. Laser Nephelometry: | | |
| Average particle diameter in nm of the nanoemulsion, determined by Gauss analysis | | 100 ± 30 |

[1] High-pressure liquid chromatography (HPLC) and enzymatic analysis
[2] Enzymatic analysis

EXAMPLE 2

Production of a 5-6% Strength Nanoemulsion with a Fatty Acid Ester 2.8 g of the amphoteric emulsifier lecithin (fat-free) in the form of unilamellar liposomes of defined vesicle size (55 nm) in an aqueous phase and 12 g of myristic acid isopropyl ester are introduced into a round flask. This aqueous phase having a volume of 250 ml is shaken by hand until the oil has been completely incorporated (visual evaluation). This preemulsion is transferred to a high-pressure homogenizer of commercially available origin and comminuted to the desired particle size of about 70 nm. Homogenization is carried out with a chamber pressure of 950 bar for 20 minutes. This process is conducted at a constant temperature of 35° C. This nanoemulsion is stable over several months. The product is characterized in Table 2 below:

TABLE 2

| | | |
|---|---|---|
| 1. Visual: | milky, opalescent, transparent in backlight | |
| 2. Chemical: | | |
| Component | Concentration (mg/ml) in Physiological Sodium Chloride Solution | |
| | Weighed Amount | Measured in Nanoemulsion |
| Lecithin | 11.2 | 11.3 ± 0.3[1] |
| Myristic acid isopropyl ester | 48.0 | 45.8 ± 2.3[2] |
| 3. Laser Nephelometry: | | |
| Average particle diameter in nm of nanoemulsion, determined by Gauss analysis | | 66 ± 27 |

[1] High-pressure liquid chromatography (HPLC) and enzymatic analysis
[2] Quantitative thin-layer chromatography (HPTLC)

Nanoemulsions produced according to the disclosed process can be utilized directly as parenteral preparations for fat alimentation.

Furthermore, it is also possible to add proteins or apoproteins to the nanoemulsions in order to form lipoprotein emulsions. On account of the small particle size, the oil-emulsifier particles display a physiological behavior analogous to the chylomicron remnants normally formed in the blood which are taken up in highly specific fashion by the liver, i.e. the hepatocytes.

The disclosed nanoemulsions exhibit physiologically a behavior like the "low-density lipoproteins" and inhibit analogously cholesterol biosynthesis in the hepatocytes.

The oil-emulsifier particles prepared by the process of this invention and, respectively, the synthetically produced lipoproteins are also specifically suited as transport vehicles for pharmaceuticals having a targeting effect in the hepatocytes.

However, the nanoemulsions can also serve as carriers for other active agents, for example for other medicinal agents and/or cosmetic ingredients. Such materials can be added to the finished nanoemulsion, or they can also be added prior to preparing the nanoemulsion to the aqueous phase or to the oil or to the emulsifier, and they are then made to attach to the oil particles and/or the emulsifier and/or are incorporated and/or dissolved therein.

Nanoemulsions containing pharmaceutically active agents can be utilized for the production of pharmaceutical preparations, the nanoemulsion being mixed, as the active component, with a solid or liquid vehicle suitable for therapeutic administration. If desired, a special galenic form can be imparted to the mixture. The following galenic forms of administration can be considered, in this connection:

- Ampoules, especially sterile injection and infusion solutions;
- solutions, especially oral liquids, eye drops and nose drops which can contain various auxiliary substances in addition to the nanoemulsion;
- aerosols without metering feature, and dosing aerosols, which can contain propellant gas and stabilizers besides the nanoemulsion;
- hydrophilic and hydrophobic gels and ointments containing the nanoemulsion;
- o/w or w/o creams containing the nanoemulsion;
- lotions and pastes containing the nanoemulsion.

Nanoemulsions produced in accordance with the process described herein can also be utilized with advantage for the preparation of nutrient solutions for cell cultures by adding to the nanoemulsions, for example, natural amino acids, antibiotics, small amounts of transferrin and optionally glucose. In such nutrient solutions, the nanoemulsions serve as energy deliverers and can at least in part replace the proteins used in conventional nutrient solutions, for example those made from calf serum.

What is claimed is:

1. Process for the production of a stable nanoemulsion of oil particles less than 200 nm in size from a triglyceride or fatty acid ester in an aqueous phase which comprises: mixing together starting materials including an aqueous phase, oil and, per part by weight of oil, 0.1 to 0.4 part by weight of an amphoteric emulsifier so as to obtain a mixture, said mixing being carried out in such a manner so that said emulsifier forms a lamellar liquid-crystalline structure in the aqueous phase, and processing the mixture into the nanoemulsion in a high-pressure homogenizer.

2. Process according to claim 1, wherein characterized the total concentration of oil and emulsifier in the aqueous phase is at most 20% by weight.

3. Process according to claim 1, wherein the emulsifier is a glycerophosphatide of the formula

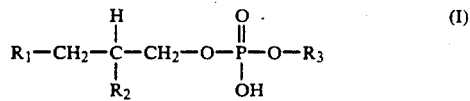

wherein $R_1$ and $R_2$ mean acyloxy and/or alkyl or alkenyl ether, and $R_3$ is tri-lower-alkyl ammonio or amino-substituted lower alkyl.

4. Process according to claim 3, wherein lecithin is used as the emulsifier.

5. Process according to claim 1, wherein the nanoemulsion is prepared at a temperature above the phase transition temperature of the emulsifier.

6. Process according to claim 1, wherein proteins or apoproteins are added to the nanoemulsion after processing in the high-pressure homogenizer, said proteins or apoproteins then attaching themselves to the oil particles so that a lipoprotein emulsion is obtained.

7. Process according to claim 1, wherein the nanoemulsion, after processing in the high-pressure homogenizer, is treated anti-microbially by pressurized steam sterilization or germ filtration.

8. Process according to claim 1, wherein an active agent or an oxygen carrier is added to the starting materials or to the mixture thereof or to the nanoemulsion after processing in the high-pressure homogenizer.

9. Process for the production of a pharmaceutical and/or cosmetic preparation which comprises: mixing together starting materials including an aqueous phase, oil and, per part by weight of oil, 0.1 to 0.4 part by weight of an amphoteric emulsifier so as to obtain a mixture, said mixing being carried out in such a manner so that said emulsifier forms a lamellar liquid-crystalline structure in the aqueous phase, processing in a high-pressure homogenizer the mixture into a stable nanoemulsion of oil particles having a size of less than 200 nm, and admixing the nanoemulsion with an inert solid or liquid vehicle suitable for a therapeutic administration so as to obtain said preparation.

10. Process according to claim 9, wherein a special galenic form is imparted to the preparation.

11. Process for the production of a nutrient solution for cell structures which comprises: mixing together starting materials including an aqueous phase, oil and, per part by weight of oil, 0.1 to 0.4 part by weight of an amphoteric emulsifier so as to obtain a mixture, said mixing being carried out in such a manner so that said emulsifier forms a lamellar liquid-crystalline structure in the aqueous phase, processing in a high-pressure homogenizer the mixture into a stable nanoemulsion of oil particles having a size of less than 200 nm, and adding to the nanoemulsion an ingredient selected from the group consisting of natural amino acids, antibiotics, and transferrin so as to obtain said nutrient solution.

* * * * *